US012778672B2

(12) United States Patent
Suarez

(10) Patent No.: US 12,778,672 B2
(45) Date of Patent: Nov. 3, 2026

(54) BASKET CATHETER WITH COMBINATION OF SPINE STRUCTURES

(71) Applicant: Biosense Webster (Israel) Ltd., Yokneam (IL)

(72) Inventor: Paul Suarez, La Crescenta, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 350 days.

(21) Appl. No.: 18/507,321

(22) Filed: Nov. 13, 2023

(65) Prior Publication Data

US 2024/0216048 A1 Jul. 4, 2024

Related U.S. Application Data

(60) Provisional application No. 63/482,697, filed on Feb. 1, 2023, provisional application No. 63/477,644, filed on Dec. 29, 2022.

(51) Int. Cl.

| | |
|---|---|
| ***A61B 18/14*** | (2006.01) |
| ***A61B 5/00*** | (2006.01) |
| *A61B 18/00* | (2006.01) |

(52) U.S. Cl.

CPC ........ *A61B 18/1492* (2013.01); *A61B 5/6858* (2013.01); *A61B 2018/0016* (2013.01); *A61B 2018/00267* (2013.01); *A61B 2018/1467* (2013.01); *A61B 2018/1475* (2013.01); *A61B 2018/1497* (2013.01)

(58) Field of Classification Search

CPC ........ A61B 2018/00267; A61B 5/6858; A61B 5/6859; A61B 2018/0016

See application file for complete search history.

(56) References Cited

U.S. PATENT DOCUMENTS

| | | | |
|---|---|---|---|
| 4,699,147 | A | 10/1987 | Chilson et al. |
| 4,940,064 | A | 7/1990 | Desai |
| 5,215,103 | A | 6/1993 | Desai |
| 5,255,679 | A | 10/1993 | Imran |
| 5,293,869 | A | 3/1994 | Edwards et al. |
| 5,309,910 | A | 5/1994 | Edwards et al. |
| 5,313,943 | A | 5/1994 | Houser et al. |

(Continued)

FOREIGN PATENT DOCUMENTS

| | | |
|---|---|---|
| CN | 111248993 A | 6/2020 |
| CN | 111248996 A | 6/2020 |

(Continued)

OTHER PUBLICATIONS

Extended European Search Report dated May 24, 2024, from corresponding European Application No. 23219842.4.

*Primary Examiner* — Jaymi E Della

(57) ABSTRACT

A basket catheter having an end effector with multiple spines can be constructed with a combination of manufacturing techniques including at least two of the following techniques: individual spines, a loop with two spines, a cut sheet, and a cut tube. A cut sheet or a cut tube can be formed to include a distal hub that has openings through which spines of one or more additional structure can pass through so that the distal hub joins distinct structures of the end effector. This provides several alternative manufacturing techniques compared to those presently used in basket catheters which rely on only one of the aforementioned manufacturing techniques.

6 Claims, 9 Drawing Sheets

(56) References Cited

U.S. PATENT DOCUMENTS 5,324,284 A 6/1994 Imran
5,345,936 A 9/1994 Pomeranz et al.
5,365,926 A 11/1994 Desai
5,391,199 A 2/1995 Ben-Haim
5,396,887 A 3/1995 Imran
5,400,783 A 3/1995 Pomeranz et al.
5,411,025 A 5/1995 Webster, Jr.
5,415,166 A 5/1995 Imran
5,443,489 A 8/1995 Ben-Haim
5,447,529 A 9/1995 Marchlinski et al.
5,456,254 A 10/1995 Pietroski et al.
5,465,717 A 11/1995 Imran et al.
5,476,495 A 12/1995 Kordis et al.
5,499,981 A 3/1996 Kordis
5,526,810 A 6/1996 Wang
5,546,940 A 8/1996 Panescu et al.
5,549,108 A 8/1996 Edwards et al.
5,558,073 A 9/1996 Pomeranz et al.
5,558,091 A 9/1996 Acker et al.
5,577,509 A 11/1996 Panescu et al.
5,595,183 A 1/1997 Swanson et al.
5,598,848 A 2/1997 Swanson et al.
5,609,157 A 3/1997 Panescu et al.
5,628,313 A 5/1997 Webster, Jr.
5,681,280 A 10/1997 Rusk et al.
5,722,401 A 3/1998 Pietroski et al.
5,722,403 A 3/1998 McGee et al.
5,725,525 A 3/1998 Kordis
5,730,128 A 3/1998 Pomeranz et al.
5,772,590 A * 6/1998 Webster, Jr. ......... A61B 5/6858 600/374
5,782,899 A 7/1998 Imran
5,823,189 A * 10/1998 Kordis .................. A61B 5/287 606/41
5,836,990 A 11/1998 Li
5,881,727 A 3/1999 Edwards
5,893,847 A 4/1999 Kordis
5,904,680 A 5/1999 Kordis et al.
5,911,739 A 6/1999 Kordis et al.
5,928,228 A 7/1999 Kordis et al.
5,935,079 A 8/1999 Swanson et al.
5,968,040 A 10/1999 Swanson et al.
6,014,579 A 1/2000 Pomeranz et al.
6,014,590 A 1/2000 Whayne et al.
6,119,030 A 9/2000 Morency
6,152,899 A * 11/2000 Farley ................ A61B 18/1492 604/113
6,172,499 B1 1/2001 Ashe
6,216,043 B1 4/2001 Swanson et al.
6,216,044 B1 4/2001 Kordis
6,239,724 B1 5/2001 Doron et al.
6,332,089 B1 12/2001 Acker et al.
6,428,537 B1 8/2002 Swanson et al.
6,456,864 B1 9/2002 Swanson et al.
6,484,118 B1 11/2002 Govari
6,569,160 B1 5/2003 Goldin et al.
6,574,492 B1 6/2003 Ben-Haim et al.
6,584,345 B2 6/2003 Govari
6,600,948 B2 7/2003 Ben-Haim et al.
6,618,612 B1 9/2003 Acker et al.
6,690,963 B2 2/2004 Ben-Haim et al.
6,738,655 B1 5/2004 Sen et al.
6,741,878 B2 5/2004 Fuimaono et al.
6,748,255 B2 6/2004 Fuimaono et al.
6,780,183 B2 8/2004 Jimenez, Jr. et al.
6,788,967 B2 9/2004 Ben-Haim et al.
6,837,886 B2 1/2005 Collins et al.
6,866,662 B2 3/2005 Fuimaono et al.
6,892,091 B1 5/2005 Ben-Haim et al.
6,970,730 B2 11/2005 Fuimaono et al.
6,973,340 B2 12/2005 Fuimaono et al.
6,980,858 B2 12/2005 Fuimaono et al.
7,048,734 B1 5/2006 Fleischman et al.
7,149,563 B2 12/2006 Fuimaono et al.
7,255,695 B2 8/2007 Falwell et al.
7,257,434 B2 8/2007 Fuimaono et al.
7,399,299 B2 7/2008 Daniel et al.
7,410,486 B2 8/2008 Fuimaono et al.
7,522,950 B2 4/2009 Fuimaono et al.
7,536,218 B2 5/2009 Govari et al.
RE41,334 E 5/2010 Beatty et al.
7,756,576 B2 7/2010 Levin
7,846,157 B2 12/2010 Kozel
7,848,787 B2 12/2010 Osadchy
7,869,865 B2 1/2011 Govari et al.
7,930,018 B2 4/2011 Harlev et al.
8,007,495 B2 8/2011 McDaniel et al.
8,048,063 B2 11/2011 Aeby et al.
8,103,327 B2 1/2012 Harlev et al.
8,167,845 B2 5/2012 Wang et al.
8,224,416 B2 7/2012 De La Rama et al.
8,235,988 B2 8/2012 Davis et al.
8,346,339 B2 1/2013 Kordis et al.
8,435,232 B2 5/2013 Aeby et al.
8,447,377 B2 5/2013 Harlev et al.
8,456,182 B2 6/2013 Bar-Tal et al.
8,498,686 B2 7/2013 Grunewald
8,517,999 B2 8/2013 Pappone et al.
8,545,490 B2 10/2013 Mihajlovic et al.
8,560,086 B2 10/2013 Just et al.
8,567,265 B2 10/2013 Aeby et al.
8,712,550 B2 4/2014 Grunewald
8,755,861 B2 6/2014 Harlev et al.
8,825,130 B2 9/2014 Just et al.
8,906,011 B2 12/2014 Gelbart et al.
8,945,120 B2 2/2015 McDaniel et al.
8,979,839 B2 3/2015 De La Rama et al.
9,037,264 B2 5/2015 Just et al.
9,131,980 B2 9/2015 Bloom
9,204,929 B2 12/2015 Solis
9,277,960 B2 3/2016 Weinkam et al.
9,314,208 B1 4/2016 Altmann et al.
9,339,331 B2 5/2016 Tegg et al.
9,486,282 B2 11/2016 Solis
9,554,718 B2 1/2017 Bar-Tal et al.
D782,686 S 3/2017 Werneth et al.
9,585,588 B2 3/2017 Marecki et al.
9,597,036 B2 3/2017 Aeby et al.
9,687,297 B2 6/2017 Just et al.
9,693,733 B2 7/2017 Altmann et al.
9,782,099 B2 10/2017 Williams et al.
9,788,895 B2 10/2017 Solis
9,801,681 B2 10/2017 Laske et al.
9,814,618 B2 11/2017 Nguyen et al.
9,833,161 B2 12/2017 Govari
9,894,756 B2 2/2018 Weinkam et al.
9,895,073 B2 2/2018 Solis
9,907,609 B2 3/2018 Cao et al.
9,974,460 B2 5/2018 Wu et al.
9,986,949 B2 6/2018 Govari et al.
9,993,160 B2 6/2018 Salvestro et al.
10,014,607 B1 7/2018 Govari et al.
10,028,376 B2 7/2018 Weinkam et al.
10,034,637 B2 7/2018 Harlev et al.
10,039,494 B2 8/2018 Altmann et al.
10,045,707 B2 8/2018 Govari
10,078,713 B2 9/2018 Auerbach et al.
10,111,623 B2 10/2018 Jung et al.
10,130,420 B2 11/2018 Basu et al.
10,136,828 B2 11/2018 Houben et al.
10,143,394 B2 12/2018 Solis
10,172,536 B2 1/2019 Maskara et al.
10,182,762 B2 1/2019 Just et al.
10,194,818 B2 2/2019 Williams et al.
10,201,311 B2 2/2019 Chou et al.
10,219,860 B2 3/2019 Harlev et al.
10,219,861 B2 3/2019 Just et al.
10,231,328 B2 3/2019 Weinkam et al.
10,238,309 B2 3/2019 Bar-Tal et al.
10,278,590 B2 5/2019 Salvestro et al.
D851,774 S 6/2019 Werneth et al.
10,314,505 B2 6/2019 Williams et al.
10,314,507 B2 6/2019 Govari et al.
10,314,648 B2 6/2019 Ge et al.

(56) References Cited

U.S. PATENT DOCUMENTS 10,314,649 B2 6/2019 Bakos et al.
10,349,855 B2 7/2019 Zeidan et al.
10,350,003 B2 7/2019 Weinkam et al.
10,362,991 B2 7/2019 Tran et al.
10,375,827 B2 8/2019 Weinkam et al.
10,376,170 B2 8/2019 Quinn et al.
10,376,221 B2 8/2019 Iyun et al.
10,398,348 B2 9/2019 Osadchy et al.
10,403,053 B2 9/2019 Katz et al.
10,441,188 B2 10/2019 Katz et al.
10,470,682 B2 11/2019 Deno et al.
10,470,714 B2 11/2019 Altmann et al.
10,482,198 B2 11/2019 Auerbach et al.
10,492,857 B2 12/2019 Guggenberger et al.
10,542,620 B2 1/2020 Weinkam et al.
10,575,743 B2 3/2020 Basu et al.
10,575,745 B2 3/2020 Solis
10,582,871 B2 3/2020 Williams et al.
10,582,894 B2 3/2020 Ben Zrihem et al.
10,596,346 B2 3/2020 Aeby et al.
10,602,947 B2 3/2020 Govari et al.
10,617,867 B2 4/2020 Viswanathan et al.
10,660,702 B2 5/2020 Viswanathan et al.
10,667,753 B2 6/2020 Werneth et al.
10,674,929 B2 6/2020 Houben et al.
10,681,805 B2 6/2020 Weinkam et al.
10,682,181 B2 6/2020 Cohen et al.
10,687,892 B2 6/2020 Long et al.
10,702,178 B2 7/2020 Dahlen et al.
10,716,477 B2 7/2020 Salvestro et al.
10,758,304 B2 9/2020 Aujla
10,765,371 B2 9/2020 Hayam et al.
10,772,566 B2 9/2020 Aujila
10,799,281 B2 10/2020 Goertzen et al.
10,842,558 B2 11/2020 Harlev et al.
10,842,561 B2 11/2020 Viswanathan et al.
10,863,914 B2 12/2020 Govari et al.
10,881,376 B2 1/2021 Shemesh et al.
10,898,139 B2 1/2021 Guta et al.
10,905,329 B2 2/2021 Bar-Tal et al.
10,912,484 B2 2/2021 Ziv-Ari et al.
10,918,306 B2 2/2021 Govari et al.
10,939,871 B2 3/2021 Altmann et al.
10,952,795 B2 3/2021 Cohen et al.
10,973,426 B2 4/2021 Williams et al.
10,973,461 B2 4/2021 Baram et al.
10,987,045 B2 4/2021 Basu et al.
11,006,902 B1 5/2021 Bonyak et al.
11,040,208 B1 6/2021 Govari et al.
11,045,628 B2 6/2021 Beeckler et al.
11,051,877 B2 7/2021 Sliwa et al.
11,109,788 B2 9/2021 Rottmann et al.
11,116,435 B2 9/2021 Urman et al.
11,129,574 B2 9/2021 Cohen et al.
11,160,482 B2 11/2021 Solis
11,164,371 B2 11/2021 Yellin et al.
2001/0029371 A1 10/2001 Kordis
2003/0233099 A1* 12/2003 Danaek .............. A61B 18/1477 606/113
2004/0210121 A1 10/2004 Fuimaono et al.
2006/0009689 A1 1/2006 Fuimaono et al.
2006/0009690 A1 1/2006 Fuimaono et al.
2006/0100669 A1 5/2006 Fuimaono et al.
2007/0093806 A1 4/2007 Desai et al.
2007/0276212 A1 11/2007 Fuimaono et al.
2008/0234564 A1 9/2008 Beatty et al.
2011/0118726 A1 5/2011 De La Rama et al.
2011/0160574 A1 6/2011 Harlev et al.
2011/0190625 A1 8/2011 Harlev et al.
2011/0213231 A1* 9/2011 Hall ...................... A61B 5/287 600/373
2011/0245756 A1 10/2011 Arora et al.
2011/0301597 A1 12/2011 McDaniel et al.
2013/0172715 A1* 7/2013 Just ...................... A61B 5/6858 606/41
2013/0172872 A1 7/2013 Subramaniam et al.
2013/0172883 A1 7/2013 Lopes et al.
2013/0178850 A1 7/2013 Lopes et al.
2013/0190587 A1 7/2013 Lopes et al.
2013/0296852 A1 11/2013 Madjarov et al.
2014/0025069 A1 1/2014 Willard et al.
2014/0052118 A1 2/2014 Laske et al.
2014/0180147 A1 6/2014 Thakur et al.
2014/0180151 A1 6/2014 Maskara et al.
2014/0180152 A1 6/2014 Maskara et al.
2014/0257069 A1 9/2014 Eliason et al.
2014/0276712 A1 9/2014 Mallin et al.
2014/0309512 A1 10/2014 Govari et al.
2015/0011991 A1 1/2015 Buysman et al.
2015/0045788 A1* 2/2015 Litscher ........... A61B 17/12104 606/41
2015/0045863 A1* 2/2015 Litscher ............. A61B 18/1492 607/116
2015/0080693 A1 3/2015 Solis
2015/0105770 A1 4/2015 Amit
2015/0119878 A1 4/2015 Heisel et al.
2015/0133760 A1* 5/2015 Kordis ................. A61B 5/6859 600/374
2015/0133919 A1 5/2015 McDaniel et al.
2015/0208942 A1 7/2015 Bar-Tal et al.
2015/0250424 A1 9/2015 Govari et al.
2015/0270634 A1 9/2015 Buesseler et al.
2015/0342491 A1* 12/2015 Marecki ............. A61B 18/1492 600/374
2015/0342532 A1 12/2015 Basu et al.
2016/0081746 A1 3/2016 Solis
2016/0113582 A1 4/2016 Altmann et al.
2016/0113709 A1 4/2016 Maor
2016/0183877 A1 6/2016 Williams et al.
2016/0228023 A1 8/2016 Govari
2016/0228062 A1 8/2016 Altmann et al.
2016/0278853 A1 9/2016 Ogle et al.
2016/0302858 A1 10/2016 Bencini
2016/0338770 A1 11/2016 Bar-Tal et al.
2016/0361111 A1* 12/2016 Seidel ................ A61B 18/1492
2017/0027638 A1 2/2017 Solis
2017/0065227 A1 3/2017 Marrs et al.
2017/0071543 A1 3/2017 Basu et al.
2017/0071544 A1 3/2017 Basu et al.
2017/0071665 A1 3/2017 Solis
2017/0095173 A1 4/2017 Bar-Tal et al.
2017/0100187 A1 4/2017 Basu et al.
2017/0143227 A1 5/2017 Marecki et al.
2017/0156790 A1 6/2017 Aujla
2017/0172442 A1 6/2017 Govari
2017/0185702 A1 6/2017 Auerbach et al.
2017/0202515 A1 7/2017 Zrihem et al.
2017/0221262 A1 8/2017 Laughner et al.
2017/0224958 A1 8/2017 Cummings et al.
2017/0265812 A1 9/2017 Williams et al.
2017/0281031 A1 10/2017 Houben et al.
2017/0281268 A1 10/2017 Tran et al.
2017/0296125 A1 10/2017 Altmann et al.
2017/0296251 A1 10/2017 Wu et al.
2017/0319140 A1* 11/2017 Wu ...................... A61B 5/6859
2017/0347959 A1 12/2017 Guta et al.
2017/0354338 A1 12/2017 Levin et al.
2017/0354339 A1 12/2017 Zeidan et al.
2017/0354364 A1 12/2017 Bar-Tal et al.
2018/0008203 A1 1/2018 Iyun et al.
2018/0028084 A1 2/2018 Williams et al.
2018/0049803 A1 2/2018 Solis
2018/0085064 A1 3/2018 Auerbach et al.
2018/0132749 A1 5/2018 Govari et al.
2018/0137687 A1 5/2018 Katz et al.
2018/0160936 A1 6/2018 Govari et al.
2018/0160978 A1 6/2018 Cohen et al.
2018/0168511 A1 6/2018 Hall et al.
2018/0184982 A1 7/2018 Basu et al.
2018/0192958 A1 7/2018 Wu
2018/0206792 A1 7/2018 Auerbach et al.
2018/0235692 A1 8/2018 Efimov et al.
2018/0249959 A1 9/2018 Osypka
2018/0256109 A1 9/2018 Wu et al.

(56) References Cited

U.S. PATENT DOCUMENTS

| | | | |
|---|---|---|---|
| 2018/0279954 | A1 | 10/2018 | Hayam et al. |
| 2018/0303414 | A1 | 10/2018 | Toth et al. |
| 2018/0310987 | A1 | 11/2018 | Altmann et al. |
| 2018/0311497 | A1 | 11/2018 | Viswanathan et al. |
| 2018/0338722 | A1 | 11/2018 | Altmann et al. |
| 2018/0344188 | A1 | 12/2018 | Govari |
| 2018/0344202 | A1 | 12/2018 | Bar-Tal et al. |
| 2018/0344251 | A1 | 12/2018 | Harlev et al. |
| 2018/0344393 | A1 | 12/2018 | Gruba et al. |
| 2018/0360534 | A1 | 12/2018 | Teplitsky et al. |
| 2018/0365355 | A1 | 12/2018 | Auerbach et al. |
| 2019/0000540 | A1 | 1/2019 | Cohen et al. |
| 2019/0008582 | A1 | 1/2019 | Govari et al. |
| 2019/0015007 | A1 | 1/2019 | Rottmann et al. |
| 2019/0030328 | A1 | 1/2019 | Stewart et al. |
| 2019/0053708 | A1 | 2/2019 | Gliner |
| 2019/0059766 | A1 | 2/2019 | Houben et al. |
| 2019/0069950 | A1 | 3/2019 | Viswanathan et al. |
| 2019/0069954 | A1 | 3/2019 | Cohen et al. |
| 2019/0117111 | A1 | 4/2019 | Osadchy et al. |
| 2019/0117303 | A1 | 4/2019 | Claude et al. |
| 2019/0117315 | A1 | 4/2019 | Keyes et al. |
| 2019/0125439 | A1 | 5/2019 | Rohl et al. |
| 2019/0133552 | A1 | 5/2019 | Shemesh et al. |
| 2019/0142293 | A1 | 5/2019 | Solis |
| 2019/0164633 | A1 | 5/2019 | Ingel et al. |
| 2019/0167137 | A1 | 6/2019 | Bar-Tal et al. |
| 2019/0167140 | A1 | 6/2019 | Williams et al. |
| 2019/0188909 | A1 | 6/2019 | Yellin et al. |
| 2019/0201664 | A1 | 7/2019 | Govari |
| 2019/0209089 | A1 | 7/2019 | Baram et al. |
| 2019/0216346 | A1 | 7/2019 | Ghodrati et al. |
| 2019/0216347 | A1 | 7/2019 | Ghodrati et al. |
| 2019/0231421 | A1 | 8/2019 | Viswanathan et al. |
| 2019/0231423 | A1 | 8/2019 | Weinkam et al. |
| 2019/0239811 | A1 | 8/2019 | Just et al. |
| 2019/0246935 | A1 | 8/2019 | Govari et al. |
| 2019/0298442 | A1 | 10/2019 | Ogata et al. |
| 2019/0314083 | A1 | 10/2019 | Herrera et al. |
| 2019/0328260 | A1 | 10/2019 | Zeidan et al. |
| 2019/0343580 | A1 | 11/2019 | Nguyen et al. |
| 2020/0000518 | A1 | 1/2020 | Kiernan et al. |
| 2020/0008705 | A1 | 1/2020 | Ziv-Ari et al. |
| 2020/0008869 | A1 | 1/2020 | Byrd |
| 2020/0009378 | A1 | 1/2020 | Stewart et al. |
| 2020/0015890 | A1 | 1/2020 | To et al. |
| 2020/0022653 | A1 | 1/2020 | Moisa |
| 2020/0029845 | A1 | 1/2020 | Baram et al. |
| 2020/0046421 | A1 | 2/2020 | Govari |
| 2020/0046423 | A1 | 2/2020 | Viswanathan et al. |
| 2020/0060569 | A1 | 2/2020 | Tegg |
| 2020/0077959 | A1 | 3/2020 | Altmann et al. |
| 2020/0093539 | A1 | 3/2020 | Long et al. |
| 2020/0129089 | A1 | 4/2020 | Gliner et al. |
| 2020/0129125 | A1 | 4/2020 | Govari et al. |
| 2020/0129128 | A1 | 4/2020 | Gliner et al. |
| 2020/0179650 | A1 | 6/2020 | Beeckler et al. |
| 2020/0196896 | A1 | 6/2020 | Solis |
| 2020/0205689 | A1 | 7/2020 | Squires et al. |
| 2020/0205690 | A1 | 7/2020 | Williams et al. |
| 2020/0205737 | A1 | 7/2020 | Beeckler |
| 2020/0205876 | A1 | 7/2020 | Govari |
| 2020/0205892 | A1 | 7/2020 | Viswanathan et al. |
| 2020/0206461 | A1 | 7/2020 | Govari et al. |
| 2020/0206498 | A1 | 7/2020 | Arora et al. |
| 2020/0289197 | A1 | 9/2020 | Viswanathan et al. |
| 2020/0297234 | A1 | 9/2020 | Houben et al. |
| 2020/0297281 | A1 | 9/2020 | Basu et al. |
| 2020/0305726 | A1 | 10/2020 | Salvestro et al. |
| 2020/0305946 | A1 | 10/2020 | DeSimone et al. |
| 2020/0397328 | A1 | 12/2020 | Altmann et al. |
| 2020/0398048 | A1 | 12/2020 | Krimsky et al. |
| 2021/0015549 | A1 | 1/2021 | Haghighi-Mood et al. |
| 2021/0022684 | A1 | 1/2021 | Govari et al. |
| 2021/0045805 | A1 | 2/2021 | Govari et al. |
| 2021/0059549 | A1 | 3/2021 | Urman et al. |
| 2021/0059550 | A1 | 3/2021 | Urman et al. |
| 2021/0059608 | A1 | 3/2021 | Beeckler et al. |
| 2021/0059743 | A1 | 3/2021 | Govari |
| 2021/0059747 | A1 | 3/2021 | Krans et al. |
| 2021/0077180 | A1 | 3/2021 | Govari et al. |
| 2021/0077184 | A1 | 3/2021 | Basu et al. |
| 2021/0082157 | A1 | 3/2021 | Rosenberg et al. |
| 2021/0085200 | A1 | 3/2021 | Auerbach et al. |
| 2021/0085204 | A1 | 3/2021 | Auerbach et al. |
| 2021/0085215 | A1 | 3/2021 | Auerbach et al. |
| 2021/0085387 | A1 | 3/2021 | Amit et al. |
| 2021/0093292 | A1 | 4/2021 | Baram et al. |
| 2021/0093294 | A1 | 4/2021 | Shemesh et al. |
| 2021/0093374 | A1 | 4/2021 | Govari et al. |
| 2021/0093377 | A1 | 4/2021 | Herrera et al. |
| 2021/0100612 | A1 | 4/2021 | Baron et al. |
| 2021/0113822 | A1 | 4/2021 | Beeckler et al. |
| 2021/0127999 | A1 | 5/2021 | Govari et al. |
| 2021/0128010 | A1 | 5/2021 | Govari et al. |
| 2021/0133516 | A1 | 5/2021 | Govari et al. |
| 2021/0145282 | A1 | 5/2021 | Bar-Tal et al. |
| 2021/0161592 | A1 | 6/2021 | Altmann et al. |
| 2021/0162210 | A1 | 6/2021 | Altmann et al. |
| 2021/0169421 | A1 | 6/2021 | Govari |
| 2021/0169550 | A1 | 6/2021 | Govari et al. |
| 2021/0169567 | A1 | 6/2021 | Govari et al. |
| 2021/0169568 | A1 | 6/2021 | Govari et al. |
| 2021/0177294 | A1 | 6/2021 | Gliner et al. |
| 2021/0177356 | A1 | 6/2021 | Gliner et al. |
| 2021/0177503 | A1 | 6/2021 | Altmann et al. |
| 2021/0178166 | A1 | 6/2021 | Govari et al. |
| 2021/0186363 | A1 | 6/2021 | Gliner et al. |
| 2021/0186604 | A1 | 6/2021 | Altmann et al. |
| 2021/0187241 | A1 | 6/2021 | Govari et al. |
| 2021/0196372 | A1 | 7/2021 | Altmann et al. |
| 2021/0196394 | A1 | 7/2021 | Govari et al. |
| 2021/0212591 | A1 | 7/2021 | Govari et al. |
| 2021/0219904 | A1 | 7/2021 | Yarnitsky et al. |
| 2021/0278936 | A1 | 9/2021 | Katz et al. |
| 2021/0282659 | A1 | 9/2021 | Govari et al. |
| 2021/0307815 | A1 | 10/2021 | Govari et al. |
| 2021/0308424 | A1 | 10/2021 | Beeckler et al. |
| 2021/0338319 | A1 | 11/2021 | Govari et al. |
| 2022/0071693 | A1 | 3/2022 | Govari et al. |
| 2022/0071696 | A1 | 3/2022 | Govari et al. |
| 2022/0087734 | A1 | 3/2022 | Govari et al. |
| 2022/0087735 | A1 | 3/2022 | Govari et al. |

FOREIGN PATENT DOCUMENTS

| | | | |
|---|---|---|---|
| EP | 0668740 | A1 | 8/1995 |
| EP | 0644738 | B1 | 3/2000 |
| EP | 0727183 | B1 | 11/2002 |
| EP | 0727184 | B1 | 12/2002 |
| EP | 2783651 | A1 | 10/2014 |
| EP | 2699151 | B1 | 11/2015 |
| EP | 2699152 | B1 | 11/2015 |
| EP | 2699153 | B1 | 12/2015 |
| EP | 2498706 | B1 | 4/2016 |
| EP | 2578173 | B1 | 6/2017 |
| EP | 3238645 | A1 | 11/2017 |
| EP | 2884931 | B1 | 1/2018 |
| EP | 2349440 | B1 | 8/2019 |
| EP | 3318211 | B1 | 12/2019 |
| EP | 3581135 | A1 | 12/2019 |
| EP | 2736434 | B1 | 2/2020 |
| EP | 3451962 | B1 | 3/2020 |
| EP | 3972510 | A1 | 3/2022 |
| WO | 9421167 | A1 | 9/1994 |
| WO | 9421169 | A1 | 9/1994 |
| WO | 9625095 | A1 | 8/1996 |
| WO | 9634560 | A1 | 11/1996 |
| WO | 0182814 | B1 | 5/2002 |
| WO | 2004087249 | A2 | 10/2004 |
| WO | 2012100185 | A2 | 7/2012 |
| WO | 2013052852 | A1 | 4/2013 |
| WO | 2013162884 | A1 | 10/2013 |
| WO | 2013173917 | A1 | 11/2013 |

(56) References Cited

FOREIGN PATENT DOCUMENTS

| | | | |
|---|---|---|---|
| WO | 2013176881 | A1 | 11/2013 |
| WO | 2014176205 | A1 | 10/2014 |
| WO | 2015187386 | A1 | 12/2015 |
| WO | 2016019760 | A1 | 2/2016 |
| WO | 2016044687 | A1 | 3/2016 |
| WO | 2017192480 | A2 | 11/2017 |
| WO | 2018111600 | A1 | 6/2018 |
| WO | 2018191149 | A1 | 10/2018 |
| WO | 2019084442 | A1 | 5/2019 |
| WO | 2019143960 | A1 | 7/2019 |
| WO | 2020026217 | A1 | 2/2020 |
| WO | 2020206328 | A1 | 10/2020 |

* cited by examiner

BASKET CATHETER WITH COMBINATION OF SPINE STRUCTURES

CROSS-REFERENCE TO RELATED APPLICATIONS

This application claims the benefit of priority to prior filed U.S. Provisional Patent Application No. 63/477,644 filed on Dec. 29, 2022 and U.S. Provisional Patent Application No. 63/482,697 filed on Feb. 1, 2023 which are hereby incorporated by reference as if set forth in full herein.

FIELD OF INVENTION

The present disclosure relates to a catheter for use in the vessel of a patient for the purpose of diagnosing or treating the patient, such as mapping tissue and/or ablating tissue using radio frequency (RF), irreversible electroporation (IRE), or other sources of energy.

BACKGROUND

Cardiac arrythmias are characterized as phenomenon that occurs when regions of cardiac tissue abnormally conduct electric signals to adjacent tissue. Examples of cardiac arrythmias can include but not be limited to atrial fibrillation, supraventricular tachyarrhythmias, and the like. Resultantly, this phenomenon can disrupt the normal cardiac cycle, thus causing asynchronous cardiac cycles or rhythms. The source of the undesired conduction of adjacent cardiac tissue can be attributed to tissue disposed in either an atria or a ventricle. Consequently, if the cardiac arrythmia remains unresolved, the unwanted signals can proliferate through the cardiac tissue, which can result in continued initiation or persistence of arrythmias.

Medical procedures to treat cardiac arrythmias generally include two steps: (1) mapping the electrical properties of the endocardium; and (2) selectively ablating cardiac tissue based on the mapped endocardium. To create the endocardium schematic, electrical activity can be measured at specific locations in the heart, which can be performed by advancing a catheter containing one or more electrical sensors into the heart to acquire the electrical activity data. Once the electrical data is obtained, the practitioner can create a schematic that can then be utilized to designate target areas where the ablation will be performed.

Regions of cardiac tissue can be mapped by a catheter to identify the abnormal electrical signals. The same or different catheter can be used to perform ablation. Some example catheters include a number of spines with electrodes positioned thereon. The electrodes are generally attached to the spines and secured in place by soldering, welding, or using an adhesive. Forming a spherical basket from the spines can be a difficult task. What is needed, therefore, are alternative devices and methods of forming a basket assembly that can help to reduce the time required for manufacturing the basket assembly and alternative basket assembly geometries in general.

SUMMARY

A basket catheter having an end effector with multiple spines can be constructed with a combination of manufacturing techniques including at least two of the following techniques: individual spines, a loop with two spines, a cut sheet, and a cut tube. A cut sheet or a cut tube can be formed to include a distal hub that has openings through which spines of one or more additional structures can pass through so that the distal hub joins distinct structures of the end effector. This provides several alternative manufacturing techniques compared to those presently used in basket catheters which rely on only one of the aforementioned manufacturing techniques.

An example end effector of a catheter can include an expandable support frame assembly and a plurality of electrodes. The expandable support frame can include a first unitary structure and a second plurality of spines separate from each other and separate from the first unitary structure. The first unitary structure can include a distal hub and a first plurality of spines extending from the distal hub of the first unitary structure. The second plurality of spines can include respective distal portions that can be coupled to the distal hub of the first unitary structure. Each respective spine of the first plurality of spines and the second plurality of spines can include a respective proximal end coupled together approximate a proximal end of the end effector. Each electrodes of the plurality of electrodes can be coupled to a respective spine of the first plurality of spines and the second plurality of spines.

The first plurality of spines and the second plurality of spines can be configured to expand away from a longitudinal axis to collectively form a basket shape.

The spines of the first plurality of spines can be positioned in an alternating pattern with spines of the second plurality of spines. The first plurality of spines can include 2, 3, 4, 5, or 6 spines. The second plurality of spines can include 2, 3, 4, 5, or 6 spines.

At least a portion of the spines of the second plurality of spines can include a respective bend in a respective distal portion. The respective bend can couple the respective distal portion to the distal hub. The respective bend can be approximately 360°. Additionally, or alternatively, at least a portion of the spines of the second plurality of spines can be coupled to the distal hub with soldering, welding, or using an adhesive.

The distal hub can include a plurality of openings therethrough wherein respective distal portions of the second plurality of spines can be disposed through openings of the distal hub.

At least a portion of the spines of the second plurality of spines can include a respective bend in the distal portion of a respective spine and approximate a respective opening of the plurality of openings through which the respective spine extends. The respective bend can couple the distal portion of the respective spine to the distal hub. The respective bend can be configured to rotate through the respective opening through which the respective spine extends.

The first unitary structure can be constructed from a planar sheet, and the distal hub can be substantially planar. Alternatively, the first unitary structure can be constructed from a tube, and the distal hub can be cylindrical.

Another example end effector of a catheter can include an expandible support frame assembly and a plurality of electrodes. The expandable support frame assembly can include a first unitary structure and a second unitary structure separate from the first unitary structure. The first unitary structure can include a distal hub and a first plurality of spines that extend from the distal hub. The second unitary structure can include a second plurality of spines that extend through one or more openings of the distal hub. Each spine of the first plurality of spines and the second plurality of spines can include a respective proximal end coupled together approximate a proximal end of the end effector.

Each of the plurality of electrodes can be coupled to a respective spine of the first plurality of spines and the second plurality of spines.

The first plurality of spines and the second plurality of spines can be configured to expand away from a longitudinal axis to collectively form a basket shape. The first plurality of spines can be positioned in an alternating pattern with spines of the second plurality of spines. The first plurality of spines can include 2, 3, 4, 5, or 6 spines and the second plurality of spines can include 2, 3, 4, 5, or 6 spines.

The first unitary structure can be constructed from a tube. The second unitary structure can be constructed from a planar sheet. The second unitary structure can include a central portion circumscribed by the distal hub. The distal hub of the first unitary structure can be cylindrical. The distal hub can include a plurality of openings such that each spine of the second plurality of spines extends from the central portion and through a respective opening of the plurality of openings of the distal hub.

Another example end effector of a catheter can include an expandable support frame assembly and a plurality of electrodes. The expandable support frame assembly can include a first unitary structure and a second plurality of spines separate from the first unitary structure. The first unitary structure can include a distal hub and a first plurality of spines extending from the distal hub. The second plurality of spines can include respective distal portions that pass through openings of the distal hub. Each respective spine of the first plurality of spines and second plurality of spines can include a respective proximal end fixed approximate a proximal end of the end effector. Each of the plurality of electrodes can be coupled to a respective spine of the first plurality of spines and of the second plurality of spines.

The first plurality of spines and the second plurality of spines can be configured to expand away from a longitudinal axis to collectively form a basket shape. Spines of the first plurality of spines can be positioned in an alternating pattern with spines of the second plurality of spines. The first plurality of spines and the second plurality of spines can include 2, 3, 4, 5, or 6 spines.

At least a portion of the spines of the second plurality of spines can include a respective bend in the distal portion of a respective spine and approximate a respective opening of the plurality of openings through which the respective spine extends, such that the respective bend can couple the distal portion of the respective spine to the distal hub. The respective bend can be approximately 360° and can be configured to rotate through the respective opening through which the respective spine extends.

The first unitary structure can be constructed from a planar sheet, and distal hub can be substantially planar. Alternatively, the first unitary structure can be constructed from a tube, and the distal hub can be cylindrical.

The second plurality of spines can include a plurality of unitary spines. Alternatively, the expandable support frame assembly can include a second unitary structure including the second plurality of spines. The second unitary structure can be constructed from a planar sheet. The second unitary structure can include a central portion circumscribed by the distal hub, such that each spine of the second plurality of spines can extend from the central portion and through a respective opening of the plurality of openings of the distal hub.

An example method of constructing a medical probe can include the following steps performed in a variety of orders and with interleaving steps as understood by a person skilled in the art. The method can include cutting a unitary structure to form a hub and a first plurality of spines extending from the hub; coupling a respective distal portion of each spine of a second plurality spines to the hub such that each spine of the second plurality of spines is unitary and separate from each other and the unitary structure; coupling a plurality of electrodes to spines of the first plurality of spines and the second plurality of spines; and affixing a respective proximal end of each spine of the first plurality of spines and the second plurality of spines at a distal end of an elongated shaft.

The method can further include configuring the first plurality of spines and the second plurality of spines to expand away from a longitudinal axis to collectively form a basket shape. The method can further include positioning the first plurality of spines in an alternating pattern with the second plurality of spines. The first plurality of spines and the second plurality of spines can include 2, 3, 4, 5, or 6 spines.

The method step of coupling the respective distal portion of each spine of the second plurality spines to the hub can further include bending the respective distal portion of one or more respective spines of the second plurality of spines about a portion of the hub. The respective bend can be approximately 360°.

The method can further include cutting openings through the hub and extending the respective distal portion of each spine of the second plurality spines through the openings.

The method step of coupling the respective distal portion of each spine of the second plurality spines to the hub can further include bending the respective distal portion of one or more respective spines of the second plurality of spines approximate a respective opening of the plurality of openings through which the respective spine extends, such that the respective bend couples the distal portion of the respective spine to the hub.

The method can further include configuring the respective bend to rotate through the respective opening through which the respective spine extends. The unitary structure may include a planar sheet. The unitary structure may include a tube.

Another example method of constructing a medical probe can include the following steps performed in a variety of orders and with interleaving steps as understood by a person skilled in the art. The method can include cutting a first unitary structure to form a hub and a first plurality of spines extending from the hub; cutting one or more openings in the hub; cutting a second unitary structure to form a central portion and a second plurality of spines extending from central portion; extending at least a portion of the second plurality of spines through the one or more openings in the hub; positioning the central portion centrally with respect to the hub; coupling a plurality of electrodes to spines of the first plurality of spines and the second plurality of spines; and affixing a respective proximal end of each spine of the first plurality of spines and the second plurality of spines at a distal end of an elongated shaft.

The method can further include configuring the first plurality of spines and the second plurality of spines to expand away from a longitudinal axis to collectively form a basket shape. The method can further include positioning the first plurality of spines in an alternating pattern with the second plurality of spines. The first plurality of spines and the second plurality of spines can include 2, 3, 4, 5, or 6 spines each. The first unitary structure can include a tube. The second unitary structure can include a planar sheet.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

The following detailed description should be read with reference to the drawings, in which like elements in different drawings are identically numbered. This description enables one skilled in the art to make and use the invention, and describes several embodiments, adaptations, variations, alternatives and uses of the invention, including what is presently believed to be the best mode of carrying out the invention. Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

When used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician. Proximal direction 88 and distal direction 87 are indicated in FIGS. 2, 3D, 4C, and 5D.

When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

Figure 1:
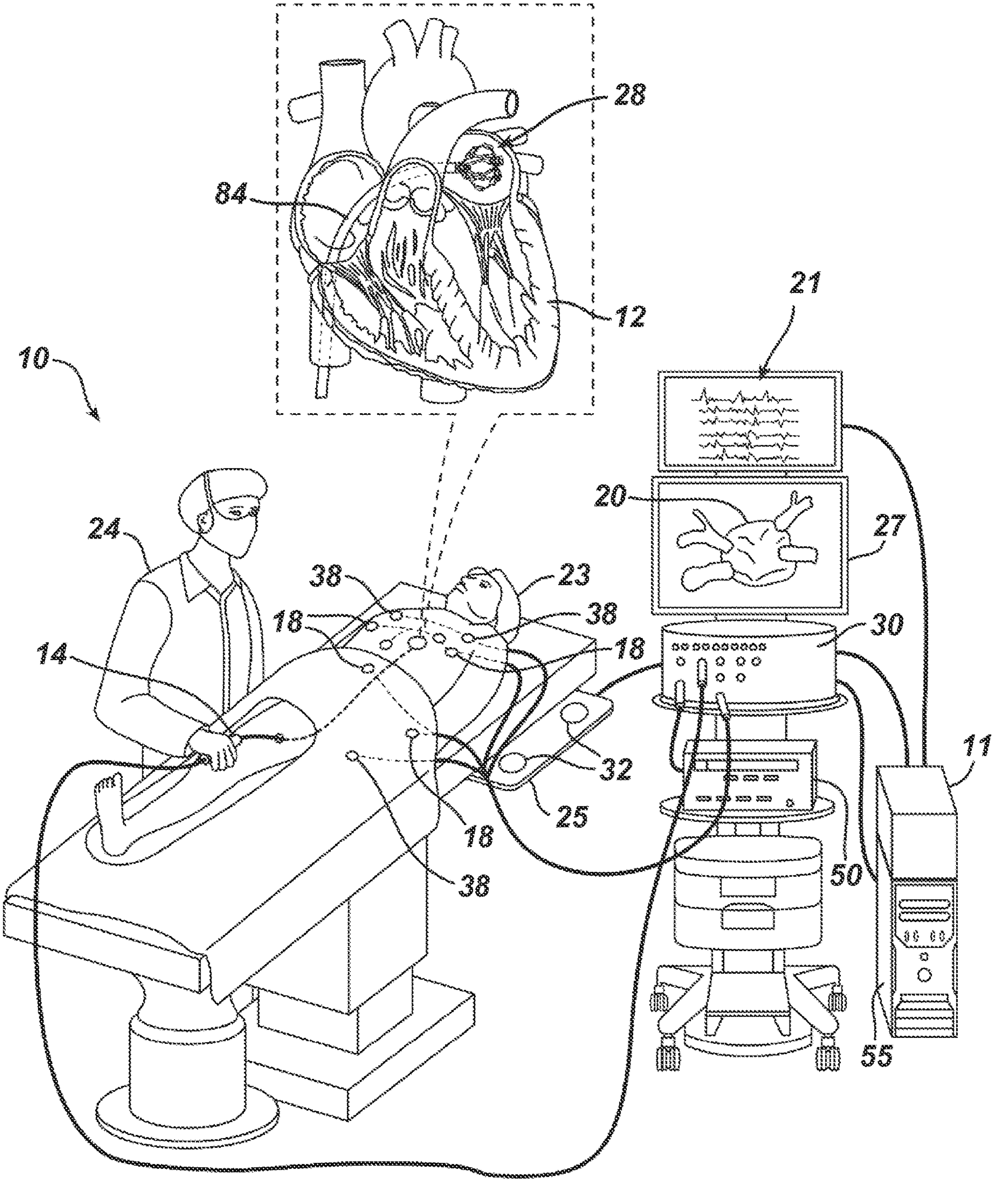
FIG. 1 is an illustration of an example catheter-based electrophysiology mapping and ablation system according to aspects of the present invention.

FIG. 1 is an illustration showing an example catheter-based electrophysiology mapping and ablation system 10. The system 10 includes multiple catheters, which are percutaneously inserted by a physician 24 through the patient's vascular system into a chamber or vascular structure of a heart 12. The illustrated catheter 14 is a basket catheter having a distal tip 28 with a basket end effector with multiple spines that can be constructed with a combination of manufacturing techniques including at least two of the following techniques: individual spines, a loop with two spines, a cut sheet, a loop with two spines, and a cut tube. A cut sheet or a cut tube can be formed to include a distal hub that has openings through which spines of one or more additional structure can pass through so that the distal hub joins distinct structures of the end effector. This provides several alternative manufacturing techniques compared to those presently used in basket catheters which rely on only one of the aforementioned manufacturing techniques.

The illustrated catheter 14 is an exemplary catheter that includes one and preferably multiple electrodes 26 optionally distributed over a plurality of spines 22 at distal tip 28 and configured to sense the IEGM signals and to deliver ablation energy. The catheter 14 includes an elongated shaft 84 that extends through vasculature and can be manipulated by the physician 24 to position the distal 28 in the desired location within the heart 12. The catheter 14 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation.

The catheter 14 can have various numbers of spines formed from various materials and including sensors and electrodes in various configurations such as disclosed in U.S. Patent Publication Nos. US2022/0071693; US2022/0071696; US2022/0087734; US2022/0087735 incorporated by reference herein and attached to the Appendix of priority patent Application No. 63/477,644 and priority Patent Application No. 63/482,697. The spines of the end effectors of the catheters of the references in the Appendix may be modified to be constructed with a combination of manufacturing techniques including at least two of the following techniques: individual spines, a loop with two spines, a cut sheet, a loop with two spines, and a cut tube as understood by a person skilled in the art. Likewise, the illustrated support structures and spines herein may be modified to include compatible features of the support structures and spines described in the Appendix as understood by a person skilled in the art.

Typically, a delivery sheath catheter is inserted into the left or right atrium near a desired location in the heart 12. Thereafter, a plurality of catheters (including the illustrated catheter 14) can be inserted into the delivery sheath catheter so as to arrive at the desired location. The plurality of catheters may include catheters dedicated for sensing Intracardiac Electrogram (IEGM) signals, catheters dedicated for ablating and/or catheters dedicated for both sensing and ablating. The physician 24 brings a distal tip 28 of the catheter 14 into contact with the heart wall for sensing a target site in the heart 12 and/or ablation at the target site.

A magnetic based position sensor 29 may be operated together with a location pad 25 including a plurality of magnetic coils 32 configured to generate magnetic fields in a predefined working volume. Real time position of a distal tip 28 of the catheter 14 may be tracked based on magnetic fields generated with a location pad 25 and sensed by a magnetic based position sensor 29. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091 incorporated by reference herein.

The system 10 includes one or more electrode patches 38 positioned for skin contact on the patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182 incorporated by reference herein.

A recorder 11 displays electrograms 21 captured with body surface ECG electrodes 18 and intracardiac electrograms (IEGM) captured with electrodes 26 of the catheter 14. The recorder 11 may include pacing capability for pacing the heart rhythm and/or may be electrically connected to a standalone pacer.

The system 10 can include an ablation energy generator 50 that is adapted to conduct ablative energy to one or more of electrodes at a distal tip of a catheter configured for ablating. Energy produced by the ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

A patient interface unit (PIU) 30 is an interface configured to establish electrical communication between catheters, electrophysiological equipment, power supply and a workstation 55 for controlling operation of system 10. Electrophysiological equipment of the system 10 may include for example, multiple catheters, a location pad 25, body surface ECG electrodes 18, electrode patches 38, an ablation energy generator 50, and a recorder 11. Optionally and preferably, the PIU 30 includes processing capability for implementing real-time computations of location of the catheters and for performing ECG calculations.

The workstation 55 includes memory, processor unit with memory or storage with appropriate operating software loaded therein, and user interface capability. The workstation 55 can be configured to provide multiple functions, optionally including (1) modeling the endocardial anatomy in three-dimensions (3D) and rendering the model or an anatomical map 20 for display on a display device 27; (2) displaying on the display device 27 activation sequences (or other data) compiled from recorded electrograms 21 in representative visual indicia or imagery superimposed on the rendered anatomical map 20; (3) displaying real-time location and orientation of multiple catheters within the heart chamber; and (4) displaying on the display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

Figure 2:
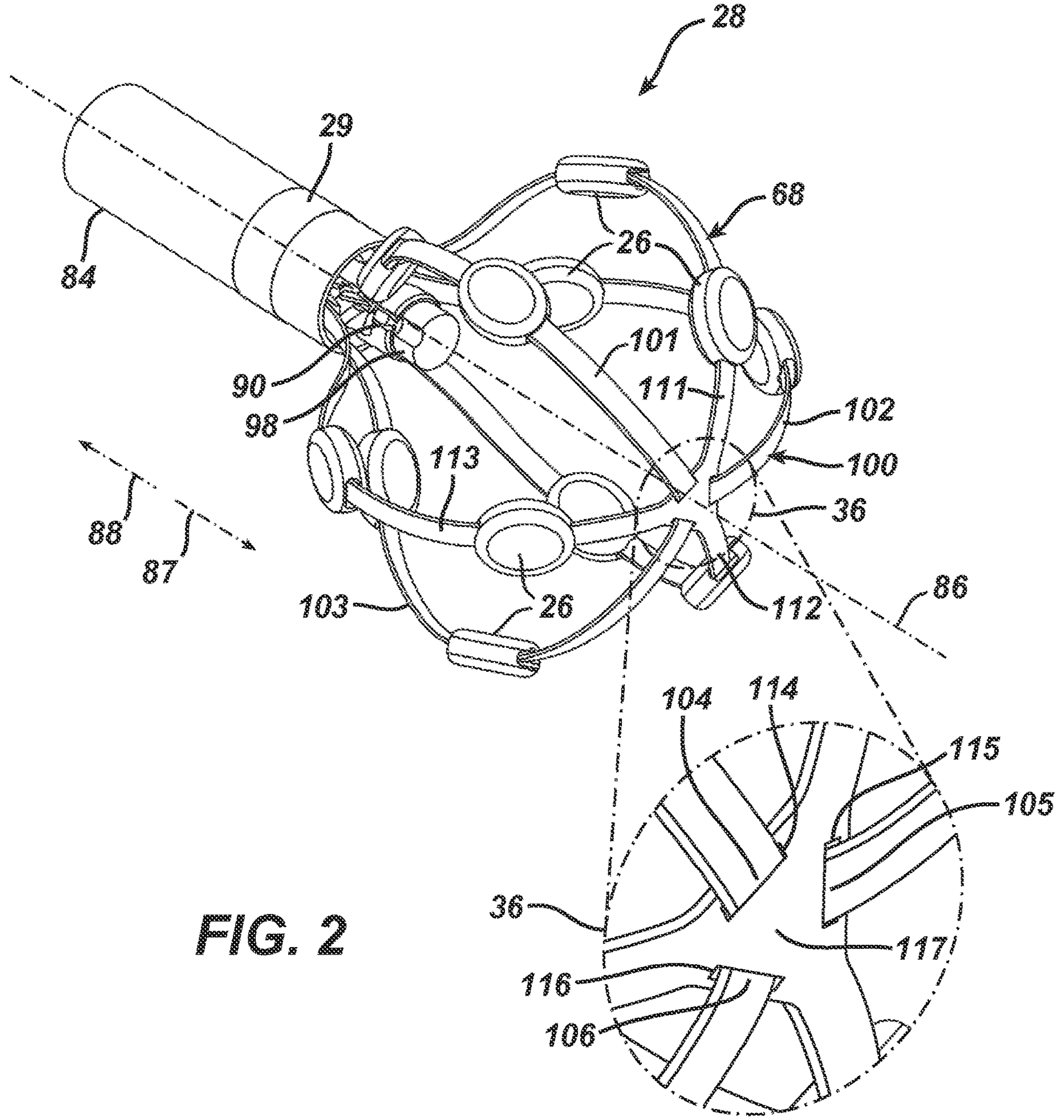
FIG. 2 is an illustration of a first example end effector of a catheter according to aspects of the present invention.

FIG. 2 is an illustration of a first example end effector of the catheter 14 including an expandable basket assembly 68 including a first example expandable support frame assembly 100 and electrodes 26 coupled to spines 101, 111, 102, 112, 103, 113 of the first example expandable support frame assembly 100. The first example expandable support frame assembly 100 includes a first unitary structure 110 and a second plurality of spines 101, 102, 103 that are separate from each other and separate from the first unitary structure 110. The first unitary structure 110 includes a distal hub 117 and first plurality of spines 111, 112, 113 that extend from the distal hub 117. The distal hub 117 is disposed at a distal end 36 of the end effector 100. The distal hub 117 is substantially planar and orthogonal to the longitudinal axis 86. The second plurality of spines 101, 102, 103 have respective distal portions 104, 105, 106 (illustrated in the detailed view of the distal end 36 of FIG. 2) that are coupled to the distal hub 117 of the first unitary structure 100.

Proximal ends of each spine 101, 111, 102, 112, 103, 113 are coupled together within the shaft 84 near a proximal end of the end effector 100 and a distal end of the shaft 84. The catheter 14 can include a spine retention hub 90 that extends longitudinally through the distal end of the tubular shaft 84. Spine retention hub 90 can include a cylindrical member can be configured to affix proximal ends of the spines 101, 111, 102, 112, 103, 113 within the shaft 84. The spine retention hub 90 can include a distal portion 98 within the basket that may include irrigation openings and/or an electrode.

The spines 101, 111, 102, 112, 103, 113 can be collapsed toward the longitudinal axis 86 so that the end effector 100 can be delivered through a sheath or intermediate catheter to a treatment site (see e.g., FIG. 1). The first example expandable support frame assembly 100 can be configured to expand to the basket shape illustrated in FIG. 2 when deployed. Preferably, the first example expandable support frame assembly 100 is self-expandable upon exiting the intermediate catheter or sheath, and may include nitinol or other shape memory material suitable to facilitate self-expansion and biocompatibility.

The first unitary structure 110 can be constructed from a planar sheet. The distal portions 104, 105, 106 of the second plurality of spines 101, 102, 103 can couple to the distal hub 117 of the first unitary structure 110 via respective openings 114, 115, 116 in the distal hub 117. Each of the respective openings 114, 115, 116 can be configured to receive the distal portions 104, 105, 106 of the second plurality of spines 101, 102, 103. The basket shape can be formed by arranging the first plurality of spines 111, 112, 113 in an alternating pattern with the second plurality of spines 101, 102, 103 and coupling the respective distal portions 104, 105, 106 of the second plurality of spines 101, 102, 103 with the respective openings 114, 115, 116 in the distal hub 117 of the planar sheet of the first unitary structure 110.

Each electrode 26 can include electrically conductive material (e.g., gold, platinum and palladium (and their respective alloys)). The basket assembly 68 includes a total of two electrodes per spine 101, 111, 102, 112, 103, 113. One skilled in the art will appreciate that various other configurations of electrodes 26 can be used with the disclosed technology without departing from the scope of this disclosure. The electrodes 26 can have a variety of shapes and can be attached to spines by a variety of means as understood by one skilled in the art.

FIGS. 3A through 3D illustrate a second example support frame assembly 200. The second example support frame assembly 200 can be used in place of the first example support frame assembly 100 in FIG. 2 to form a catheter similar to the catheter 14 illustrated in FIG. 1.

Figure 3A:
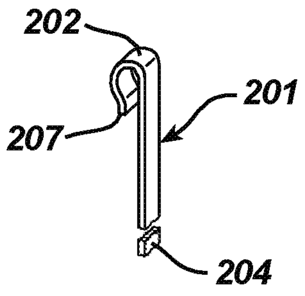
FIGS. 3A, 3B, 3C, and 3D are illustrations of a features of a second example end effector of a catheter according to aspects of the present invention.

FIG. 3A illustrates an individual spine 201 having a proximal end 204 and a bend 202 near a distal spine end 207 of the spine 201. The bend 202 is approximately 360°, although an angle less than 360° (e.g. between 180° and 360°) may be sufficient, or a kink (similar to kink 902 in FIG. 9) may be used in place of bend 202.

Figure 3B:
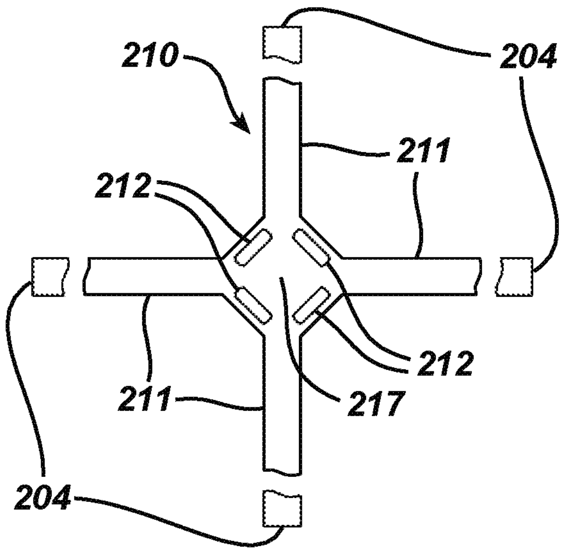

FIG. 3B illustrates a unitary structure formed from a planar sheet 210 cut to include spines 211 and a distal hub 217 with openings 212 sized to receive the distal end 207 and bend 202 of the individual spine 201.

Figure 3C:
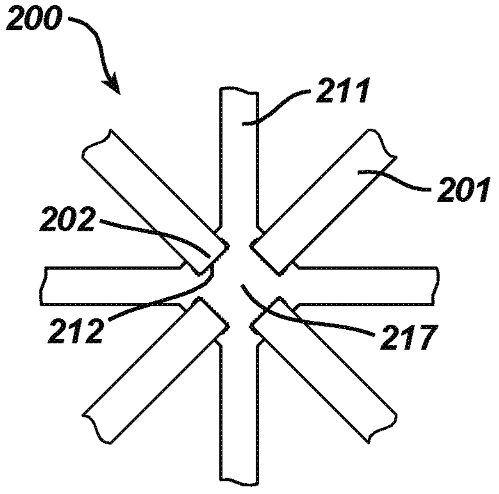

FIG. 3C illustrates four individual spines 201 (FIG. 3A) coupled to the planar sheet 210 (FIG. 3B). The spines 211 of the planar sheet 210 are in an alternating arrangement with the individual spines 201. To couple the individual spines 201 to the openings 212 of the distal hub 217 of the planar sheet 210, the spine distal end 207 is inserted in a respective opening 212, and the individual spine 201 is aligned so that the spine distal end 207 is positioned proximally along the individual spine 201 in relation to the bend 202. The individual spine 201 can be pre-bent, and the individual spine 201 can be rotated about the bend 202 as the individual spine 201 is attached to the distal hub 217. Alternatively, the individual spine 201 can be bent after the spine distal end 207 is inserted into a respective opening 212, thereby forming bend 202.

Figure 3D:
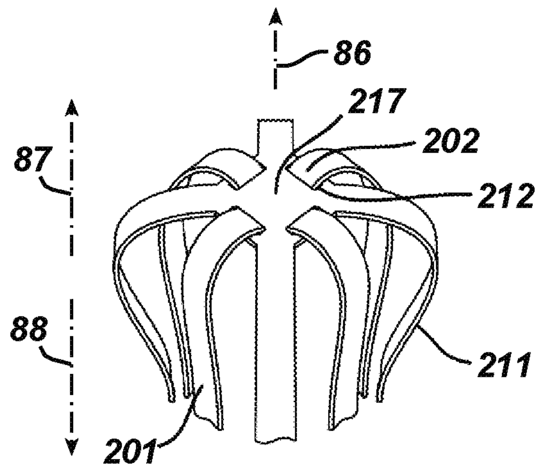

FIG. 3D illustrates the second example support frame assembly 200 shaped to form a basket similar to the support frame 100 illustrated in FIG. 2. The distal hub 217 is substantially planar and is perpendicular to the longitudinal axis 86.

Note that the first example support frame assembly 100 illustrated in FIG. 2 includes a total of six spines while the second example support frame assembly 200 illustrated in FIGS. 3A through 3D include a total of eight spines. The second example support frame assembly 200 can be modified to include six spine; and conversely, the first example support frame assembly 100 can be modified to include eight spines. The individual spines 101, 102, 103 of the first example support frame assembly 100 can be attached to the distal hub 117 similar to how the individual spines 201 are attached to the distal hub 217 as illustrated in FIGS. 3A through 3D.

The bend 202 can be configured to rotate through the respective opening 212, which can be advantageous as it can facilitate movement of the individual spines 201 between a collapsed configuration during delivery and a basket shape when deployed. The respective bend of the individual spines 201 can be approximately 360°, however the degree of curvature for the respective bend of the individual spines 201 is not so limited. It should also be appreciated that the degree of curvature for the respective bend between each of the individual spines 201 can vary to allow for enduring couplings with various support structures.

Figure 4A:
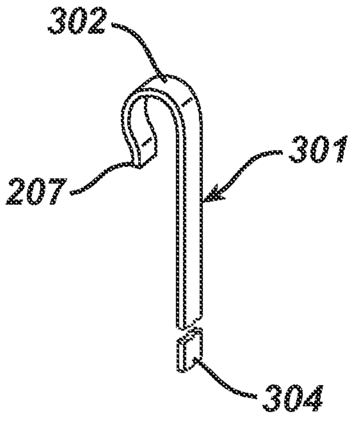
FIGS. 4A, 4B, and 4C are illustrations of a third example end effector of a catheter according to aspects of the present invention.
Figure 4B:
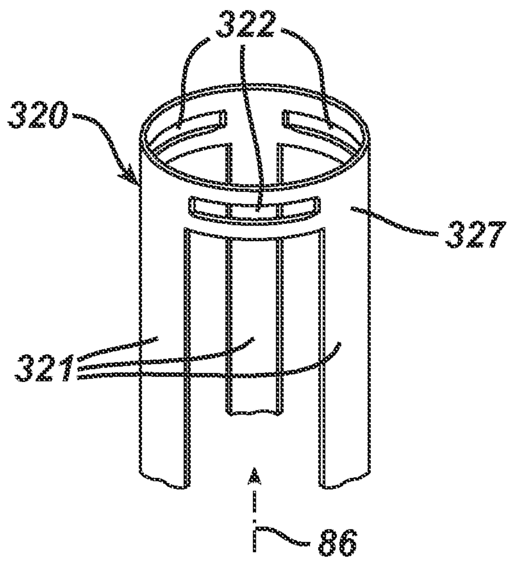
Figure 4C:
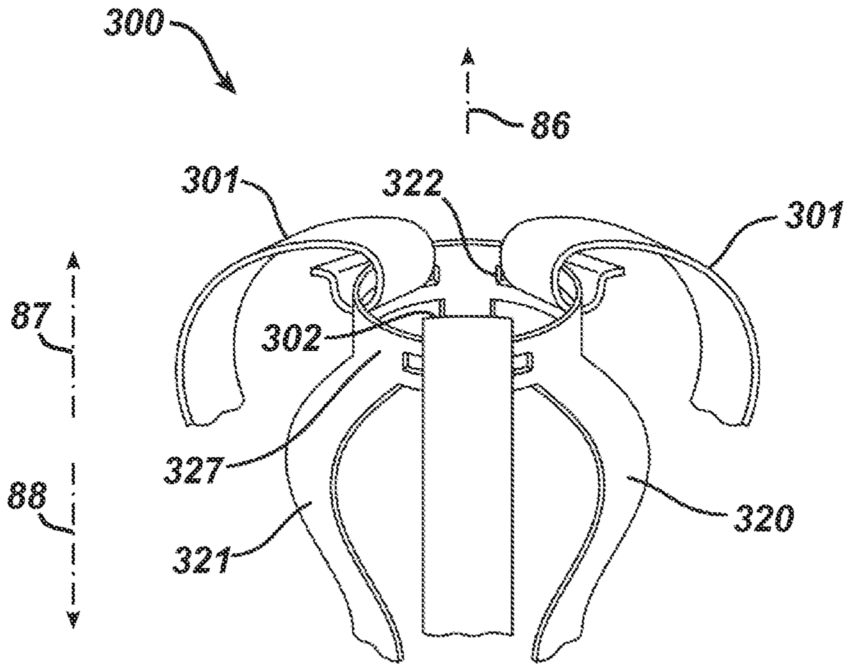

FIGS. 4A through 4C illustrate a third example support frame assembly 300. The third example support frame assembly 300 can be used in place of the first example support frame assembly 100 in FIG. 2 to form a catheter similar to the catheter 14 illustrated in FIG. 1.

FIG. 4A illustrates an individual spine 301 having a proximal end 304 and a bend 302 near a distal spine end 307 of the spine 301. The individual spine 301 illustrated in FIG. 4A is configured similarly to the individual spine 201 illustrated in FIG. 3A. The bend 302 is approximately 360°, although an angle less than 360° (e.g. between 180° and 360°) may be sufficient, or a kink (similar to kink 902 in FIG. 9) may be used in place of bend 302.

FIG. 4B illustrates a unitary structure formed from a tube 320 cut to include spines 321 and a distal hub 327 with openings 322 sized to receive the distal end 307 and bend 302 of the individual spine 301. The distal hub 327 is cylindrical about the longitudinal axis 86.

FIG. 4C illustrates four individual spines 301 (FIG. 4A) coupled to the tube 320 (FIG. 4B) and shaped to form a basket shape. The spines 321 of the tube 320 are in an alternating arrangement with the individual spines 301. To couple the individual spines 301 to the openings 322 of the distal hub 327 of the tube 320, the spine distal end 307 is inserted in a respective opening 322, and the spine is aligned so that the spine distal end 307 is positioned proximally along the spine 301 in relation to the bend 302. The individual spine 302 can be pre-bent, and the individual spine 301 can be rotated about the bend 302 as the individual spine 301 is attached to the distal hub 327. Alternatively, the individual spine 301 can be bent after the spine distal end 307 is inserted into a respective opening 322, thereby forming bend 302.

The tube 320 is oriented such that the spines 321 of the tube 320 extend from a proximal side of the cylindrical distal hub 327. Alternatively, the spines 321 of the tube 320 can be inverted so that the spines 321 of the tube extend from a distal side of the cylindrical distal hub 327 similar to the tube 420 illustrated in FIG. 5D.

To couple the individual spines 301 to the openings 322 of the distal hub 327 of the tube 320, the spine distal end 307 is inserted in a respective opening 322, and the individual spine 301 is aligned so that the spine distal end 307 is positioned proximally along the individual spine 301 in relation to the bend 302. The individual spine 301 can be pre-bent, and the individual spine 301 can be rotated about the bend 302 as the individual spine 301 is attached to the distal hub 327. Alternatively, the individual spine 301 can be bent after the spine distal end 307 is inserted into a respective opening 322, thereby forming bend 302.

The bend 302 can be configured to rotate through the respective opening 322, which can be advantageous as it can facilitate movement of the individual spines 301 between a collapsed configuration during delivery and a basket shape when deployed. The respective bend of the individual spines 301 can be approximately 360°, however the degree of curvature for the respective bend of the individual spines 301 is not so limited. It should also be appreciated that the degree of curvature for the respective bend between each of the individual spines 301 can vary to allow for enduring couplings with various support structures.

The individual spines 301 and tube spines 321 may be arranged in an alternating pattern arrangement, circumferentially about the distal hub 327. The alternating pattern arrangement of the tube spines 321 and the individual spines 301 the third example support frame assembly 300.

FIGS. 5A through 5D are illustrations of a fourth example support frame assembly 400. The fourth example support frame assembly 400 can be used in place of the first example support frame assembly 100 in FIG. 2 to form a catheter similar to the catheter 14 illustrated in FIG. 1.

Figure 5A:
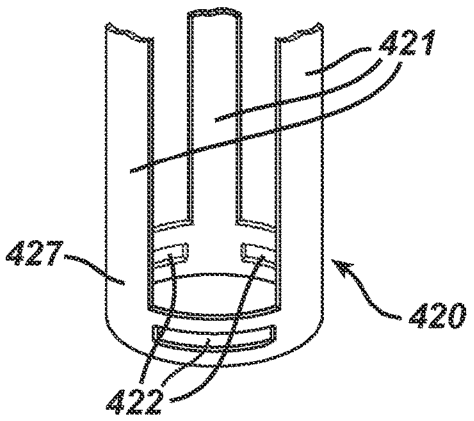
FIGS. 5A, 5B, 5C, and 5D are illustrations of a fourth example end effector of a catheter according to aspects of the present invention.

FIG. 5A illustrates a first unitary structure formed from a tube 420 cut to include a first plurality of spines 421 extending from a distal hub 427. The tube 420 illustrated in FIG. 5A is configured similarly to the tube 320 illustrated in FIG. 4B. The distal hub 427 includes openings 422 configured to receive spines 411 of a second unitary structure 410 (FIG. 5B).

Figure 5B:
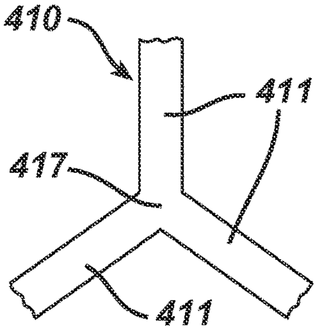

FIG. 5B illustrates the second unitary structure formed from a planar sheet 410 cut to include a second plurality of spines 422 extending from a central hub 417.

Figure 5C:
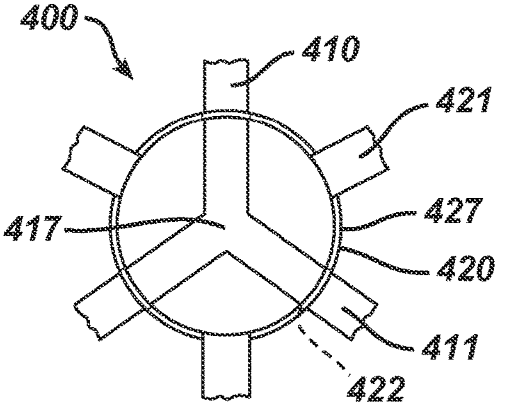

FIG. 5C illustrates the second plurality of spines 411 of the planar sheet 410 inserted through the openings 422 of the tube 420, thereby coupling the first unitary structure to the second unitary structure. The intersection of the tube 420 and the planar sheet 410 can be disposed at the distal end 36 (FIG. 2) of the end effector.

Figure 5D:
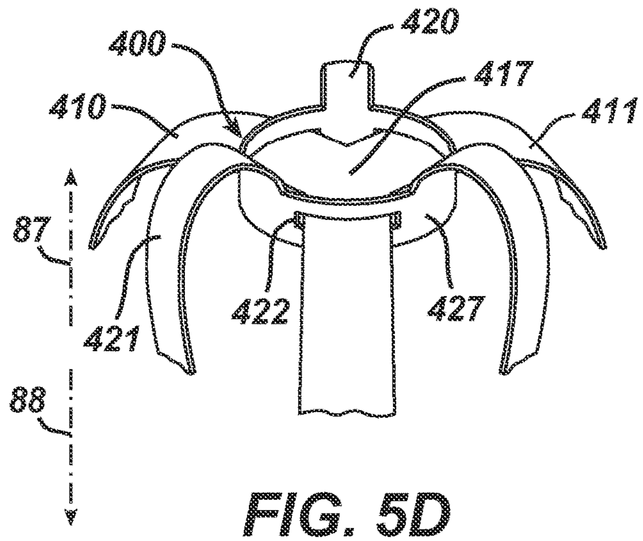

FIG. 5D illustrates the first plurality of spines 421 and the second plurality of spines 411 can be arranged in an alternating pattern circumferentially about the distal hub 427, which can be configured to form the fourth example expandable support frame assembly 400, which may resemble a basket shape. The tube 420 is oriented such that the first plurality of spines 421 of the tube 420 are inverted and extend from a distal side of the cylindrical distal hub 427. Alternatively, the spines 421 of the tube 420 can extend from a proximal side of the cylindrical distal hub 427 similar to the tube 320 illustrated in FIG. 4D. The inverted configuration may result in an atraumatic distal end of the fourth example expandable support frame assembly 400.

Figure 6:
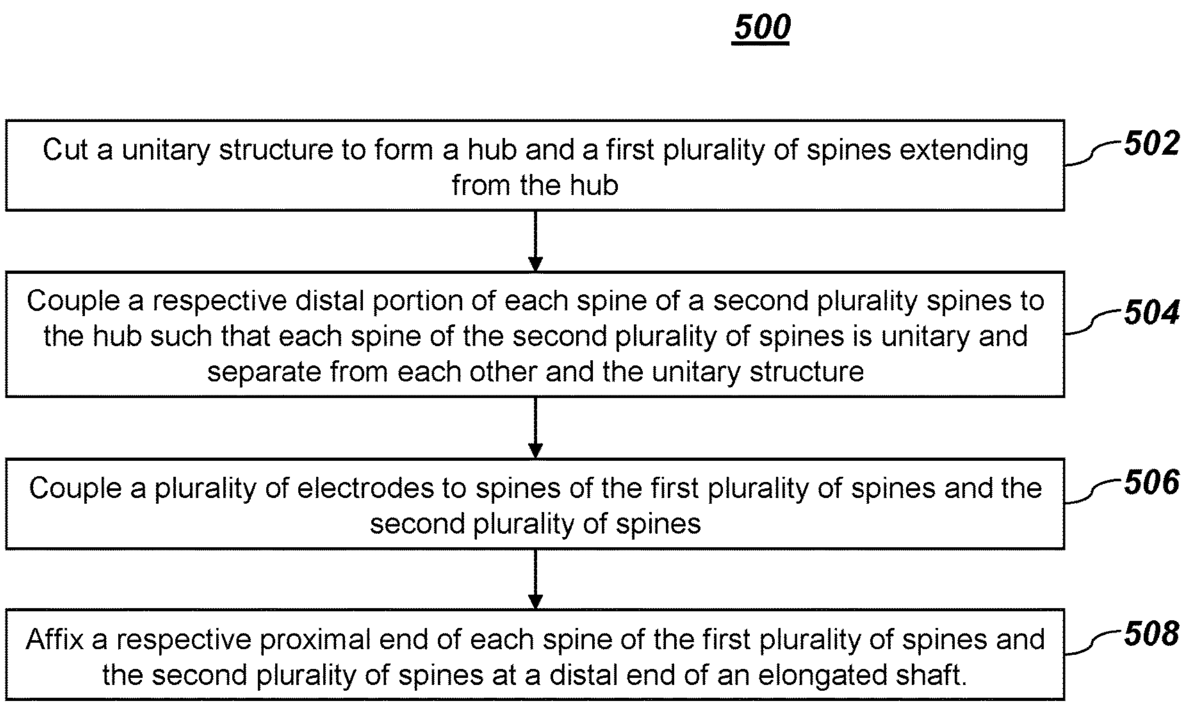
FIG. 6 is a method flow diagram for a method of manufacture of an example end effector of a catheter according to aspects of the present invention.

FIG. 6 illustrates a method flow chart including a method 500 of manufacture for an end effector as illustrated in FIGS. 1 and 2 and including a support frame assembly 100, 200, 300 configured such as illustrated in FIGS. 3A through 3D or FIGS. 4A through 4C.

At step 502, a unitary structure can be cut to form a hub and a first plurality of spines extending from the hub. For example, as shown in FIG. 2, FIG. 3A-D, or FIG. 4A-C, the hub may be constructed from a planar sheet or a tube. When constructed from a tube, the hub can have a cylindrical shape.

At step 504, a respective distal portion of each spine of a second plurality of spines can be coupled to the hub such that each spine of the second plurality of spines is unitary and separate from each other and the unitary structure. As shown in FIG. 4A (and similarly in FIG. 3A), each of the individual spines 301 may have a respective bend located at the spine distal end 302. The respective bend can be used to couple each spine distal end 302 of the individual spines 301 to the distal ring 327 by rotating each spine distal end through the openings for spine distal ends 322, which is illustrated in FIG. 4C (and similarly in FIG. 3C).

At step 506, a plurality of electrodes can be coupled to the first plurality of spines and the second plurality of spines. The electrodes can be configured similarly to electrodes 26 illustrated herein, variations thereof, and alternatives thereto as understood by a person skilled in the art.

At step 508, a respective proximal end of each spine of the first plurality of spines and the second plurality of spines can be affixed at a distal end of an elongated shaft.

Figure 7:
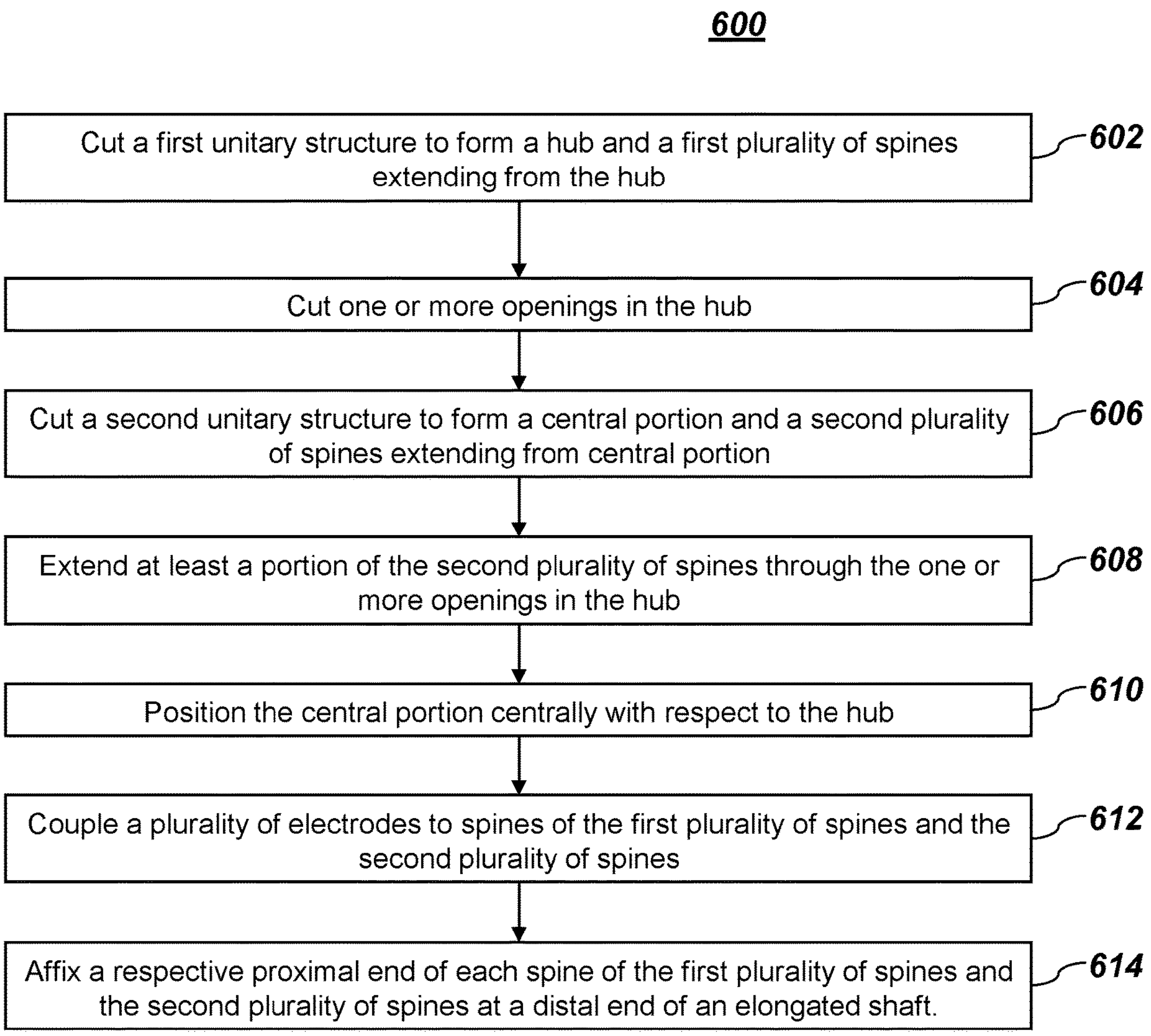
FIG. 7 is a method flow diagram for another method of manufacture for an example end effector of a catheter according to aspects of the present invention.

FIG. 7 illustrates a method flow chart including a method 600 of manufacture for an end effector as illustrated in FIGS. 5A through 5D.

At step 602, a first unitary structure can be cut to form a hub and a first plurality of spines extending from the hub. The first unitary structure can include a tube such as the tube 421 illustrated in FIGS. 5A, 5C, and 5D, variations thereof, and alternatives thereto as understood by a person skilled in the pertinent art.

At step 604, one or more openings can be cut into the hub. As illustrated in FIG. 5A, the distal hub 427 of the tube 420 can include openings 422 oriented circumferentially about the distal hub 427, which may be configured to receive a plurality of spines.

At step 606, a second unitary structure can be cut to form a central portion and a second plurality of spines extending from the central portion. As shown in FIG. 5B, the second unitary structure can resemble a planar sheet 410 that can include a central portion 417, wherein the central portion 417 can include a plurality of sheet spines 411 that can extend from the central portion 417.

At step 608, at least a portion of the second plurality of spines can be extended through the one or more openings in the hub. As shown in FIGS. 5C and 5D, the planar sheet 410 can be juxtaposed within the distal hub 427 that can be constructed from the tube 420 by extending the plurality of sheet spines 411 through the openings 422 of the distal hub 427.

At step 610, the central portion can be aligned with respect to the hub. As illustrated in FIGS. 5C and 5D, the central portion 417 of the planar sheet 410 can be aligned with respect to the distal hub 427 of the tube 420.

At step 612, a plurality of electrodes can be coupled to spines of the first plurality of spines and second plurality of spines. The plurality of electrodes 26, as shown in FIG. 2, are offered to illustrate various configurations of electrodes 26 that can be used with the end effector but should not be construed as limiting. One skilled in the art will appreciate that various other configurations of electrodes 40 can be used with the disclosed technology without departing from the scope of this disclosure.

At step 614, a respective proximal end of each spine of the first plurality of spines and the second plurality of spines can be affixed at a distal end of an elongated shaft. The respective proximal portions of the tube spines 421 and the respective proximal portions of the sheet spines 411 can be configured to couple together approximate a proximal end of the end effector, which can be disposed approximate the distal end of the catheter shaft 84 similar to the illustration shown in FIG. 2.

FIGS. 8A, 8B, 8C, and 8D are illustrations of a fifth example support frame assembly 700. The fifth example support frame assembly 700 can be used in place of the first example support frame assembly 100 in FIG. 2 to form a catheter similar to the catheter 14 illustrated in FIG. 1.

Figure 8A:
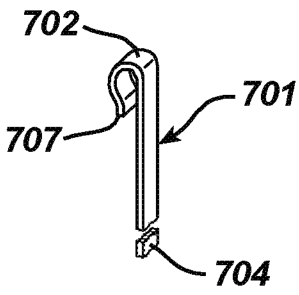
FIGS. 8A, 8B, 8C, and 8D are illustrations of a fifth example end effector of a catheter according to aspects of the present invention.

FIG. 8A illustrates an individual spine 701 having a proximal end 704 and a bend 702 near a distal spine end 707 of the spine 701. The bend 702 is approximately 360°, although an angle less than 360° (e.g. between 180° and 360°) may be sufficient, or a kink (similar to kink 902 in FIG. 9) may be used in place of bend 702.

Figure 8B:
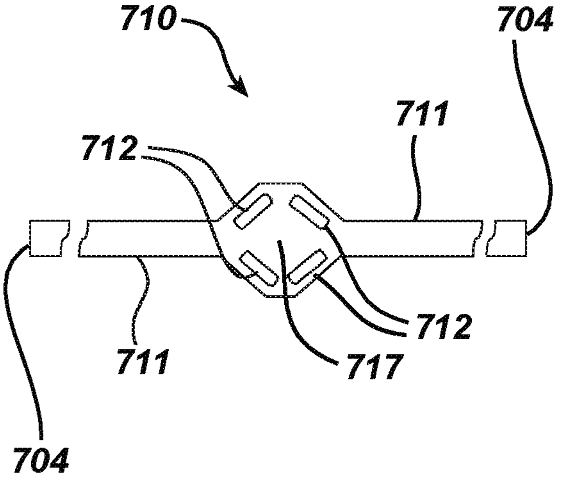

FIG. 8B illustrates a unitary structure formed from a strip or a planar sheet 710 cut to include two spines 711 and a distal hub 717 with openings 712 sized to receive the distal end 707 and bend 702 of the individual spine 701. The unitary structure includes exactly two spines that can be curved to form a single loop in the support frame assembly 700 (FIG. 8D) such that the unitary structure forms a loop with two spines.

Figure 8C:
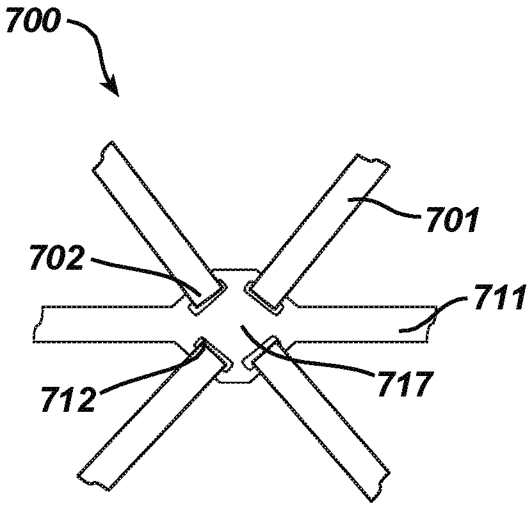

FIG. 8C illustrates four individual spines 701 coupled to the loop 710. To couple the individual spines 701 to the openings 712 of the distal hub 717 of the loop 710, the spine distal end 707 is inserted in a respective opening 712, and the individual spine 701 is aligned so that the spine distal end 707 is positioned proximally along the individual spine 701 in relation to the bend 702. The individual spine 701 can be pre-bent, and the individual spine 701 can be rotated about the bend 702 as the individual spine 701 is attached to the distal hub 717. Alternatively, the individual spine 701 can be bent after the spine distal end 707 is inserted into a respective opening 712, thereby forming bend 702.

Figure 8D:
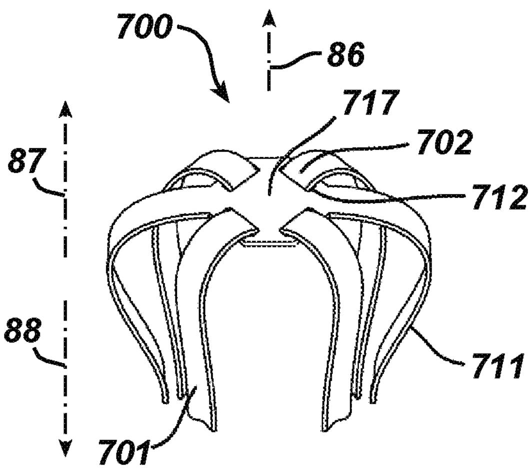

FIG. 8D illustrates the fifth example support frame assembly 700 shaped to form a basket similar to the support frame 100 illustrated in FIG. 2. The distal hub 717 is substantially planar and is perpendicular to the longitudinal axis 86.

Figure 9A:
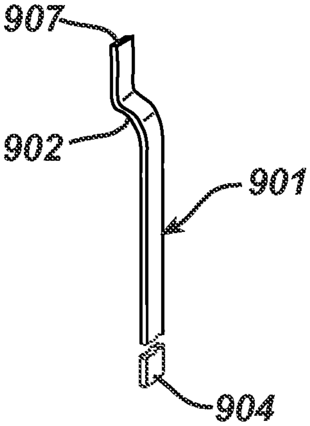
FIGS. 9A, 9B, and 9C are illustrations of an alternative spine configured with additional example end effectors according to aspects of the present invention.
Figure 9B:
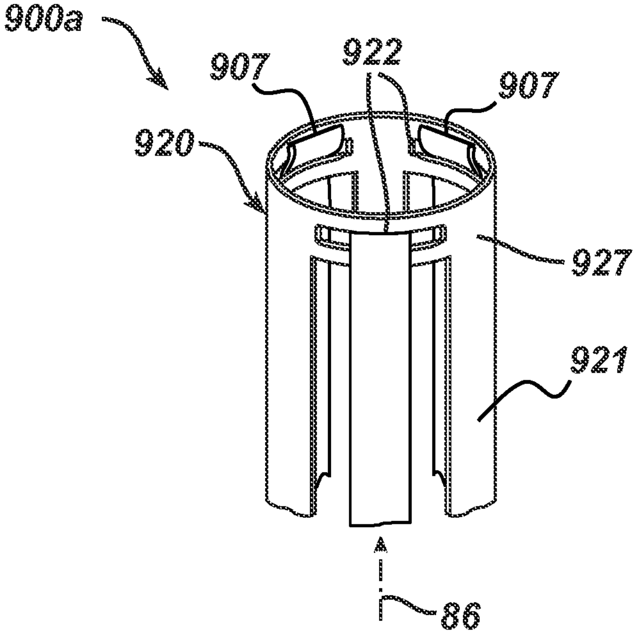
Figure 9C:
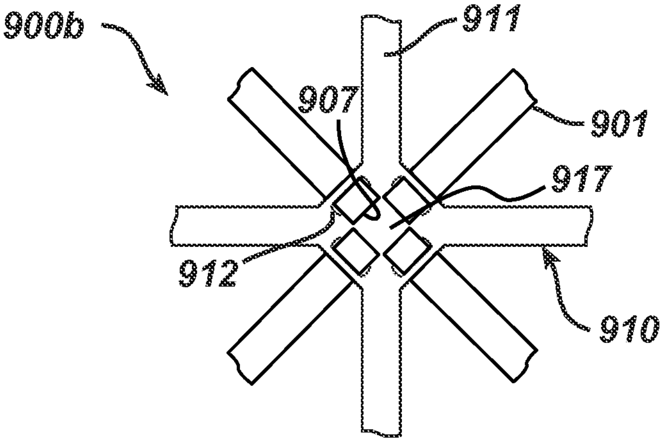

FIGS. 9A, 9B, and 9C are illustrations of an alternative spine 901 configured with additional support frame assemblies 900*a*, 900*b* that can be used in place of the first example support frame assembly 100 in FIG. 2 to form a catheter similar to the catheter 14 illustrated in FIG. 1.

FIG. 9A illustrates an individual spine 901 having a proximal end 904, a distal end 907, and a kink 902 near the distal end 907. The kink 902 is shaped to facilitate coupling of the individual spine 901 to a distal hub of a unitary structure to form a support frame assembly.

FIG. 9B illustrates spines 901, similar to the spine 901 in FIG. 9A, coupled to a tubular unitary structure 920 with a distal hub 927 and spines 921 extending from the distal hub 927 to form a sixth example support frame assembly 900*a*. The distal hub 927 includes openings 922 sized to receive the distal ends 907 of the spines 901. The kink 902 in the individual spines 901 passes through a respective opening 922 in the distal hub 927. The distal end 907 (spine portion distal of the kink 902) can be coupled to the distal hub 927 with soldering, welding, or using an adhesive.

FIG. 9C illustrates spines 901, similar to the spine 901 in FIG. 9A, coupled to a planar unitary structure 910 with a distal hub 917 and spines 911 extending from the distal hub 917 to form a seventh example support frame assembly 900*b*. The distal hub 917 includes openings 912 sized to receive the distal ends 907 of the spines 901. The kink 902 in the individual spines 901 passes through a respective opening 912 in the distal hub 917. The distal end 907 (spine portion distal of the kink 902) can be coupled to the distal hub 917 with soldering, welding, or using an adhesive.

The following clauses list non-limiting embodiments of the disclosure:

Clause 1. An end effector of a catheter, the end effector comprising: an expandable support frame assembly comprising a first unitary structure and a second plurality of spines separate from each other and separate from the first unitary structure, the first unitary structure comprising a distal hub and a first plurality of spines extending from the distal hub, the second plurality of spines comprising respective distal portions coupled to the distal hub of the first unitary structure, and each respective spine of the first plurality of spines and the second plurality of spines comprising a respective proximal end coupled together approximate a proximal end of the end effector; and a plurality of electrodes each coupled to a respective spine of the first plurality of spines and of the second plurality of spines.

Clause 2. The end effector of clause 1, the first plurality of spines and the second plurality of spines being configured to expand away from a longitudinal axis to collectively form a basket shape.

Clause 3. The end effector of clause 1 or 2, spines of the first plurality of spines being positioned in an alternating pattern with spines of the second plurality of spines.

Clause 4. The end effector of any one of clauses 1-3, the first plurality of spines consisting of 2, 3, 4, 5, or 6 spines, and the second plurality of spines consisting of 2, 3, 4, 5, or 6 spines.

Clause 5. The end effector of any one of clauses 1-4, at least a portion of the spines of the second plurality of spines comprising a respective bend in a respective distal portion coupling, and the respective bend coupling the respective distal portion to the distal hub.

Clause 6. The end effector of clause 5, the respective bend being approximately 360°.

Clause 7. The end effector of any one of clauses 1-6, the distal hub comprising a plurality of openings therethrough, and wherein respective distal portions of the second plurality of spines are disposed through openings of the distal hub.

Clause 8. The end effector of clause 7, at least a portion of the spines of the second plurality of spines comprising a respective bend in the distal portion of a respective spine and approximate a respective opening of the plurality of openings through which the respective spine extends such that the respective bend couples the distal portion of the respective spine to the distal hub.

Clause 9. The end effector of clause 8, the respective bend being configured to rotate through the respective opening through which the respective spine extends.

Clause 10. The end effector of any one of clauses 1-9, the first unitary structure being constructed from a planar sheet.

Clause 11. The end effector of any one of clauses 1-10, the distal hub being substantially planar.

Clause 12. The end effector of any one of clauses 1-9, the first unitary structure being constructed from a tube.

Clause 13. The end effector of any one of clauses 1-9 or 12, the distal hub being cylindrical.

Clause 14. An end effector of a catheter, the end effector comprising: an expandable support frame assembly comprising a first unitary structure and a second unitary structure separate from the first unitary structure, the first unitary structure comprising a distal hub and a first plurality of spines extending from the distal hub, the second unitary structure comprising a second plurality of spines extending through one or more openings of the distal hub, and each respective spine of the first plurality of spines and the second plurality of spines comprising a respective proximal end coupled together approximate a proximal end of the end effector; and a plurality of electrodes each coupled to a respective spine of the first plurality of spines and of the second plurality of spines.

Clause 15. The end effector of clause 14, the first plurality of spines and the second plurality of spines being configured to expand away from a longitudinal axis to collectively form a basket shape.

Clause 16. The end effector of clause 13 or 14, spines of the first plurality of spines being positioned in an alternating pattern with spines of the second plurality of spines.

Clause 17. The end effector of any one of clauses 13-16, the first plurality of spines consisting of 2, 3, 4, 5, or 6 spines, and the second plurality of spines consisting of 2, 3, 4, 5, or 6 spines.

Clause 18. The end effector of any one of clauses 13-17, the first unitary structure being constructed from a tube.

Clause 19. The end effector of any one of clauses 13-18, the distal hub being cylindrical.

Clause 20. The end effector of any one of clauses 13-19, the second unitary structure being constructed from a planar sheet.

Clause 21. The end effector of any one of clauses 13-20, the second unitary structure comprising a central portion circumscribed by the distal hub.

Clause 22. The end effector of any one of clauses 21, the distal hub comprising a plurality of openings such that each spine of the second plurality of spines extends from the central portion and through a respective opening of the plurality of openings of the distal hub.

Clause 23. An end effector of a catheter, the end effector comprising: an expandable support frame assembly comprising a first unitary structure and a second plurality of spines separate from the first unitary structure, the first unitary structure comprising a distal hub and a first plurality of spines extending from the distal hub, the second plurality of spines comprising respective distal portions passing through openings of the distal hub, and each respective spine of the first plurality of spines and the second plurality of spines comprising a respective proximal end fixed approximate a proximal end of the end effector; and a plurality of electrodes each coupled to a respective spine of the first plurality of spines and of the second plurality of spines.

Clause 24. The end effector of clause 23, the first plurality of spines and the second plurality of spines being configured to expand away from a longitudinal axis to collectively form a basket shape.

Clause 25. The end effector of clause 23 or 24, spines of the first plurality of spines being positioned in an alternating pattern with spines of the second plurality of spines.

Clause 26. The end effector of any one of clauses 23-25, the first plurality of spines consisting of 2, 3, 4, 5, or 6 spines, and the second plurality of spines consisting of 2, 3, 4, 5, or 6 spines.

Clause 27. The end effector of any one of clauses 23-26, at least a portion of the spines of the second plurality of spines comprising a respective bend in the distal portion of a respective spine and approximate a respective opening of the plurality of openings through which the respective spine extends such that the respective bend couples the distal portion of the respective spine to the distal hub.

Clause 28. The end effector of clause 27, the respective bend being approximately 360°.

Clause 29. The end effector of clause 27 or 28, the respective bend being configured to rotate through the respective opening through which the respective spine extends.

Clause 30. The end effector of any one of clauses 23-29, the second plurality of spines comprising a plurality of unitary spines.

Clause 31. The end effector of any one of clauses 23-30, the first unitary structure being constructed from a planar sheet.

Clause 32. The end effector of any one of clauses 23-31, the distal hub being substantially planar.

Clause 33. The end effector of any one of clauses 23-30, the first unitary structure being constructed from a tube.

Clause 34. The end effector of any one of clauses 23-30 or 33, the distal hub being cylindrical.

Clause 35. The end effector of any one of clauses 23-26, the expandable support frame assembly comprising a second unitary structure comprising the second plurality of spines.

Clause 36. The end effector of clause 35, the first unitary structure being constructed from a tube.

Clause 37. The end effector of clause 35 or 36, the distal hub being cylindrical.

Clause 38. The end effector of any one of clauses 35-37, the second unitary structure being constructed from a planar sheet.

Clause 39. The end effector of any one of clauses 35-38, the second unitary structure comprising a central portion circumscribed by the distal hub such that each spine of the second plurality of spines extends from the central portion and through a respective opening of the plurality of openings of the distal hub.

Clause 40. A method of constructing a medical probe, the method comprising: cutting a unitary structure to form a hub and a first plurality of spines extending from the hub; coupling a respective distal portion of each spine of a second plurality spines to the hub such that each spine of the second plurality of spines is unitary and separate from each other and the unitary structure; coupling a plurality of electrodes to spines of the first plurality of spines and the second plurality of spines; and affixing a respective proximal end of each spine of the first plurality of spines and the second plurality of spines at a distal end of an elongated shaft.

Clause 41. The method of clause 40, further comprising: configuring the first plurality of spines and the second plurality of spines to expand away from a longitudinal axis to collectively form a basket shape.

Clause 42. The method of clause 40 or 41, further comprising: positioning the first plurality of spines in an alternating pattern with the second plurality of spines.

Clause 43. The method of any one of clauses 40-42, the first plurality of spines consisting of 2, 3, 4, 5, or 6 spines, and the second plurality of spines consisting of 2, 3, 4, 5, or 6 spines.

Clause 44. The method of any one of clauses 40-43, wherein coupling the respective distal portion of each spine of the second plurality spines to the hub further comprises bending the respective distal portion of one or more respective spines of the second plurality of spines about a portion of the hub.

Clause 45. The method of clause 44, the respective bend being approximately 360°.

Clause 46. The method of any one of clauses 40-45, further comprising: cutting openings through the hub; and extending the respective distal portion of each spine of the second plurality spines through the openings.

Clause 47. The method of clause 46, wherein coupling the respective distal portion of each spine of the second plurality spines to the hub further comprises bending the respective distal portion of one or more respective spines of the second plurality of spines approximate a respective opening of the plurality of openings through which the respective spine extends such that the respective bend couples the distal portion of the respective spine to the hub.

Clause 48. The method of clause 47, further comprising: configuring the respective bend to rotate through the respective opening through which the respective spine extends.

Clause 49. The method of any one of clauses 40-48, the unitary structure comprising a planar sheet.

Clause 50. The method of any one of clauses 40-48, the unitary structure comprising a tube.

Clause 51. A method of constructing a medical probe, the method comprising: cutting a first unitary structure to form a hub and a first plurality of spines extending from the hub; cutting one or more openings in the hub; cutting a second unitary structure to form a central portion and a second plurality of spines extending from central portion; extending at least a portion of the second plurality of spines through the one or more openings in the hub; positioning the central portion centrally with respect to the hub; coupling a plurality of electrodes to spines of the first plurality of spines and the second plurality of spines; and affixing a respective proximal end of each spine of the first plurality of spines and the second plurality of spines at a distal end of an elongated shaft.

Clause 52. The method of clause 51, further comprising: configuring the first plurality of spines and the second plurality of spines to expand away from a longitudinal axis to collectively form a basket shape.

Clause 53. The method of clause 51 or 52, further comprising: positioning the first plurality of spines in an alternating pattern with the second plurality of spines.

Clause 54. The method of any one of clauses 51-53, the first plurality of spines consisting of 2, 3, 4, 5, or 6 spines, and the second plurality of spines consisting of 2, 3, 4, 5, or 6 spines.

Clause 55. The method of any one of clauses 51-54, the first unitary structure comprising a tube.

Clause 56. The method of any one of clauses 51-55, the second unitary structure comprising a planar sheet.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

What is claimed is:

1. An end effector of a catheter, the end effector comprising:

an expandable support frame assembly comprising a first unitary structure and a second unitary structure separate from the first unitary structure, the first unitary structure comprising a distal hub and a first plurality of spines extending from the distal hub, the distal hub comprising a plurality of openings therethrough alternating in a circumferential direction with the first plurality of spines, a full perimeter of each opening of the plurality of openings defined inward from an edge of the distal hub, and the second unitary structure comprising a central portion circumscribed by the distal hub and a second plurality of spines extending through one or more openings of the plurality of openings of the distal hub, each spine of the second plurality of spines extending from the central portion and through a respective opening of the plurality of openings of the distal hub, and each respective spine of the first plurality of spines and the second plurality of spines comprising a respective proximal end coupled together approximate a proximal end of the end effector; and a plurality of electrodes each coupled to one respective spine from a combined plurality of spines comprising the first plurality of spines and the second plurality of spines.

2. The end effector of claim 1, the first plurality of spines and the second plurality of spines being configured to expand away from a longitudinal axis to collectively form a basket shape.

3. The end effector of claim 1, spines of the first plurality of spines being positioned in an alternating pattern with spines of the second plurality of spines.

4. The end effector of claim 1, the first plurality of spines selected from the group consisting of 2, 3, 4, 5, or 6 spines, and the second plurality of spines selected from the group consisting of 2, 3, 4, 5, or 6 spines.

5. The end effector of claim 1, the first unitary structure being constructed from a tube and the distal hub being cylindrical.

6. The end effector of claim 1, the second unitary structure being constructed from a planar sheet.

* * * * *